United States Patent [19]

Aid et al.

[11] 4,218,313
[45] Aug. 19, 1980

[54] DIALYSIS APPARATUS AND TECHNIQUE

[75] Inventors: James D. Aid, St. Petersburg, Fla.; Kyu H. Lee, King of Prussia, Pa.

[73] Assignee: Extracorporeal Medical Specialties, Inc., King of Prussia, Pa.

[21] Appl. No.: 827,565

[22] Filed: Aug. 25, 1977

Related U.S. Application Data

[63] Continuation-in-part of Ser. No. 799,582, May 23, 1977, abandoned.

[51] Int. Cl.² .......................... B01D 3/00; B01D 13/00
[52] U.S. Cl. .................................. 210/22 A; 73/149; 210/87; 210/95; 210/321 B
[58] Field of Search ................. 210/22, 87, 90, 321 B, 210/232, 541, 188, 95; 73/37, 149, 200, 323

[56] References Cited

U.S. PATENT DOCUMENTS

| | | | |
|---|---|---|---|
| 3,669,880 | 6/1972 | Marantz et al. | 210/22 |
| 3,844,940 | 10/1974 | Kopf et al. | 210/321 BX |
| 3,946,731 | 3/1976 | Lichtenstein | 210/90 |
| 3,976,574 | 8/1976 | White | 210/188 |
| 3,990,973 | 11/1976 | Boag et al. | 210/321 BX |
| 4,021,341 | 5/1977 | Cosentino et al. | 210/87 |

Primary Examiner—Frank A. Spear, Jr.

[57] ABSTRACT

Dialysis apparatus is arranged to enable convenient measuring of ultrafiltration rate from liquid, such as blood, that is to be dialyzed. Dialyzer can have, downstream of a dialysis chamber, a dialyzate passageway through which the ultrafiltration flow rate can be readily measured as by introducing a gas bubble into the dialyzate and timing its movement through the passageway. An air-injection attachment can be fitted to the dialyzer or to a dialyzate supply system, to inject the gas bubble for such measurement. Bubble injection can also be effected in a flow rate measuring passageway downstream of the dialyzer. Flow rates of dialyzate into and out of dialyzer can be compared to show ultrafiltration while dialyzing.

6 Claims, 8 Drawing Figures

DIALYSIS APPARATUS AND TECHNIQUE

CROSS-REFERENCE TO RELATED APPLICATION

This application is in part a continuation of application Ser. No. 799,582 filed May 23, 1977, now abandoned.

BRIEF SUMMARY OF THE INVENTION

The present invention relates to dialysis apparatus and techniques for making and using such apparatus.

Among the objects of the present invention is the provision of improved dialysis apparatus that is simple to manufacture and adaptable for use in different ways.

Additional objects of the present invention include the provision of novel techniques for making and using dialysis apparatus.

The foregoing as well as further objects of the present invention will be more fully understood from the following description of several of its exemplifications, reference being made to the accompanying drawings wherein:

DETAILED DESCRIPTION

According to the present invention ultrafiltration through a dialysis unit is readily measured by providing the unit with an externally viewable dialyzate flow passageway downstream of a dialysis chamber, arranging for that passageway to be sufficiently empty to enable accurate reading of the level of a liquid moving through it, circulating through the dialysis unit a liquid to be dialyzed, introducing liquid in the dialyzate passageway so as to partially fill it, holding the dialysis unit so that the liquid level in the passageway moves along the length of the passageway as ultrafiltration takes place, and timing the movement of that level.

The partial filling of the measurement passageway is very effectively accomplished by first essentially filling it with dialyzate, and then introducing a quantity of gas into it.

The dialysis unit preferably has the measurement passageway built into it, and it is also desirable to apply marks on the unit to show spaced liquid levels in that passageway and thus simplify the measurement. A series of spaced marks can be used so that the measurement of level travel can be started at different points and/or can be made two or more times while the level makes one traverse.

A very desirable measuring passageway has a cross-sectional area of about $\frac{1}{8}$ to about 3 square centimeters for every square meter of dialysis membrane surface in the chamber, where blood is the liquid to be dialyzed. Measurement times can then be at least about 30 seconds long so that they are accurately determined, while liquid level movement is neither too fast to follow nor too slow and uncertain.

The ultrafiltration measurement of the present invention is easily arranged with the help of an attachment that has a standard dialyzate connector by which it can be connected to the dialyzate inlet of a dialyzer, a gas injector communicating with the connector, and a valve that closes such communication except when gas is introduced into the dialyzate inlet. The attachment can also have a second standard dialyzate connector by which it can be connected to dialyzate supply equipment.

Alternatively the dialyzate supply equipment can be arranged to have a shut-off valve in its dialyzate outlet conduit as well as gas-introducing means connected to the conduit downstream of the shut-off valve.

A particularly desirable dialysis unit for use in accordance with the present invention is constructed along the lines of those described in FIGS. 9 through 12 of application Ser. No. 629,082 filed Nov. 5, 1975 and subsequently abandoned. It is however preferred to modify that construction. Thus the end caps preferably have a cap wall closure at least about 2 millimeters thick and gasketing which has its external aspect vented to the outside. The preferred wall thickness improves the ultrasonic welding of the cap to the casing, and the vent simplifies the testing of the unit.

Figure 1:
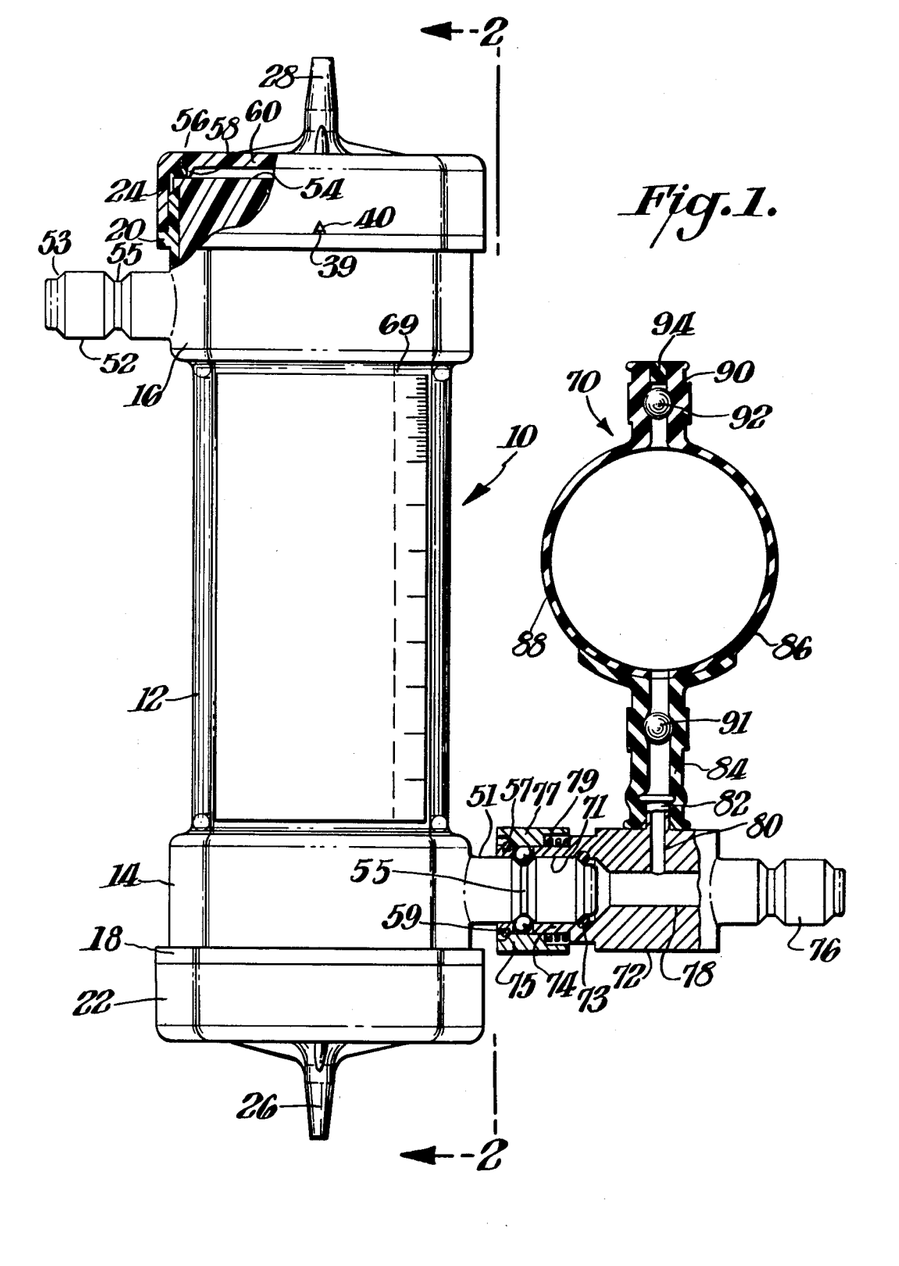
FIG. 1 is a front elevation, partly in section, of a dialyzer combination pursuant to the present invention.
Figure 2:
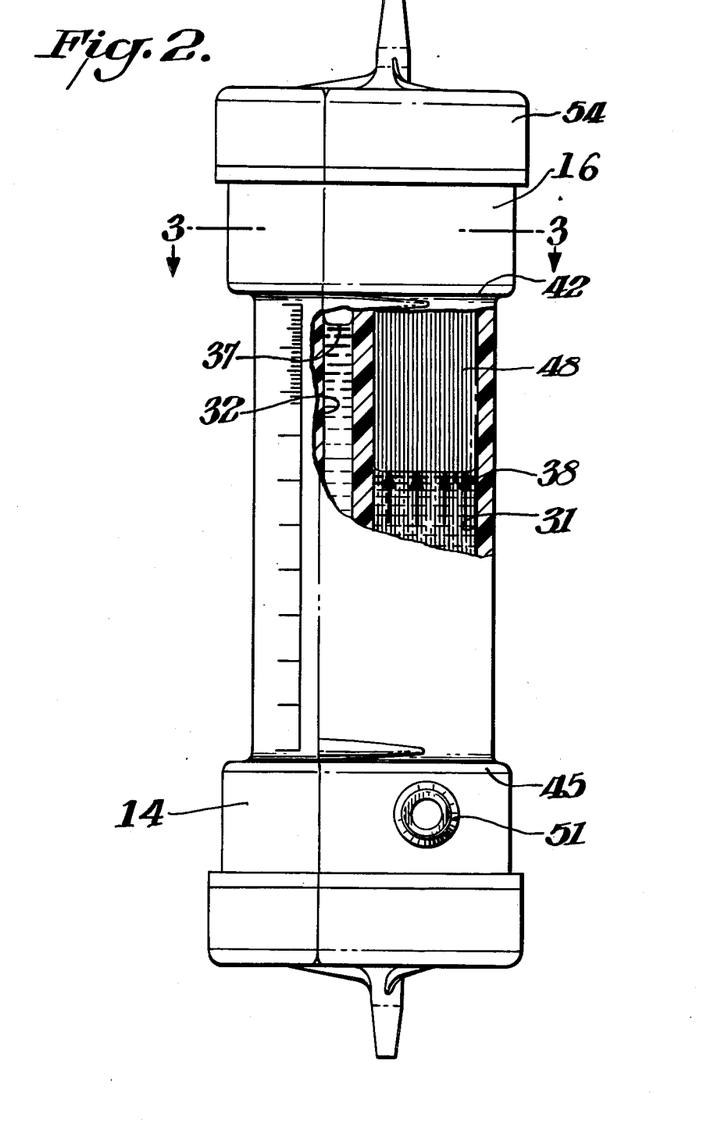
FIG. 2 is a view generally along the line 2—2 of FIG. 1, illustrating the internal operation of the dialyzer.
Figure 3:
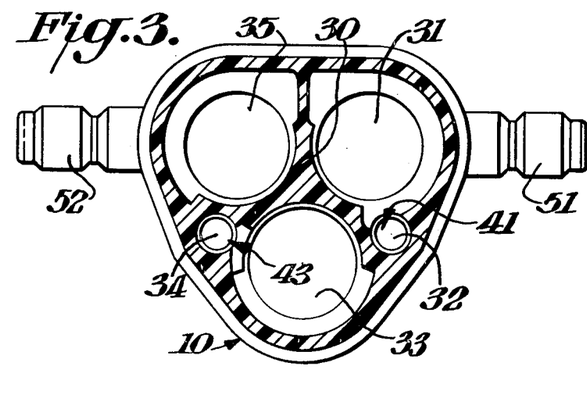
FIG. 3 is a sectional view of the dialyzer of FIG. 2 taken along line 3—3, further illustrating its operation.

Turning now to the accompanying drawings, FIGS. 1, 2 and 3 illustrate various details of the present invention. A dialyzer 10 has a plastic casing 12 of polystyrene for example with enlarged header end portions 14, 16, securing flanges 18 and 20 encircling each end portion. Ultrasonically welded to each flange is a plastic cap 22, 24 that covers the casing ends and has a central nipple 26, 28 for introducing the liquid to be dialyzed at one end and removing it at the other. The caps can be made of the same plastic as the casing.

The interior of the casing contains partitioning that subdivides it into a plurality of chambers and passageways extending longitudinally through it, as more clearly seen in FIG. 3 and in the patent application Ser. No. 629,082. Thus partitioning 30 subdivides the interior of the casing into three large-bore chambers 31, 33 and 35 as well as two small-bore passageways 32, 34. The chambers and passageways extend the length of the casing and are only interconnected near the casing ends. Near the upper end a port 41 in the partitioning 30 establishes communication between the upper portions of chamber 31 and passageway 32. A similar port (not shown) in the lower portion of the partitioning establishes communication between the lower portions of passageway 32 and chamber 33, a third port 43 in the upper portion of the partitioning establishes communication between the upper portions of chamber 33 and passageway 34, and a fourth port (also not shown) at the lower portion of the partitioning establishes communication between the lower portions of passageway 34 and chamber 35.

A dialyzate inlet connector 51 is molded integrally with the enlarged lower end portion 14 of the casing and opens into the lower portion of chamber 31 while a dialyzate outlet connector 52 correspondingly provided in the upper enlarged casing end portion 16 opens into the upper portion of chamber 35 to complete the dialyzate flow path.

A bundle of hollow dialysis fibers 48 is inserted in each chamber 31, 33, 35, the fibers extending the length of the casing. At or near each casing end the fibers are potted in an end wall 54 of a sealing resin that can project somewhat from the casing end as illustrated in FIG. 1. End caps can be sealed against these end walls by gaskets such as O-rings 56 shown in FIG. 1 as fitted between short flanges 58 projecting from the body 60 of each end cap.

Potting resin 54 which can be a polyurethane, leaves the hollow interiors of the fibers 48 open so that the liquid to be dialyzed flows through these fibers, preferably countercurrent to the flow of the dialyzate in chambers 31, 33 and 35. Thus blood or other liquid to be dialyzed can be introduced through upper nipple 28 and withdrawn from lower nipple 26, while dialyzate is introduced into connector 51 and withdrawn through connector 52. The dialyzate flows upwardly through chamber 31 around and between the individual fibers in that chamber, then down through passageway 32, after which it flows upwardly through chamber 33 around and between the individual fibers there, then descends through passageway 34 for a final pass upwardly through chamber 35 around and between the individual fibers there. From the upper portion of chamber 35 the dialyzate flows out of the dialyzer 10 through the outlet connector 52.

The casing 12 is made of transparent plastic like polystyrene so that the contents of passageways 32, 34 as well as their side walls are clearly seen from outside the casing. Chambers 31, 33 and 35 are also seen from outside the casing, but these chambers are essentially filled with the hollow dialysis fibers 48, and when a dark liquid like blood is being dialyzed there isn't much detail that can be made out visually other than the presence or absence of gas bubbles in front of the fibers.

In one embodiment of the present invention the lengths of chambers 31, 33 and 35 between the enlarged casing ends 14, 16 are cylindrical with diameters of about 2⅛ centimeters so that each chamber can be packed with something over 3,000 hollow fibers to provide a total membrane dialysis surface of about 1 square meter per dialyzer or about ⅓ square meter per chamber. The passageways 32, 34 in this embodiment are cylindrical with diameters of about ¾ to about 4/5 centimeter. So dimensioned the standard dialyzate flow rates of 300 or 500 milliliters per minute will be rapid enough to flush out of the dialyzer essentially all gas bubbles that may appear in the dialyzate as the dialyzate passes through it.

For measuring the rate of ultrafiltration taking place in the dialyzer a volume of gas such as air is deliberately introduced into the dialyzate contained in the dialyzer. To this end FIG. 1 shows a gas-injecting attachment 70 that has a body 72 carrying a standard dialyzate connector 74, which connector is fitted to the dialyzer's dialyzate intake connector 51. Body 72 also carries another standard dialyzate connector 76 for connection to the dialyzate supply output of a source of dialyzate, and a bore 78 that establishes communication between the two connectors 74, 76.

Connector 74 is shown as of the female type having a socket 71 that receives connector 51, and an O-ring seal 73 against which a tapered tip 53 on connector 51 seats. Connector 51 is latched in sealing engagement with the O-ring by a set of balls 75 held in apertures around the wall of socket 71 and forced into a groove 55 in connector 51 by a slide ring 77. The engagement is unlatched by sliding the slide ring toward the body 72 against the resistance of a spring 79, far enough to bring a relieved internal taper 57 of the slide around the balls thus permitting the balls to be moved outwardly in a radial direction into the wall of socket 71 when the connectors are pulled apart. A locking snap ring 59 can be snapped into a groove on the outer face of the socket 71 to keep the slide ring 77 from coming off the connector when in use, but permitting disassembly when desired.

Also communicating with bore 78 is a branch 80 that leads to a nipple 82 projecting from the surface of body 72 and onto which is frictionally mounted a plastic or rubber outlet tube 84 of a gas injector 86. This injector has a squeezable bulb 88 secured as by cementing or welding to tube 84, and carrying an air inlet tube 90. Valves 91, 92 in tubes 84 and 90 control the air injection action, and a filter such as a plug 94 of foamed plastic or rubber can be used to make sure solid particles are kept out of the entering air.

Valves 91, 92 can be of any desired type, but are shown as balls of relatively inert material such as stainless steel very snugly held in encircling seats molded into thick-walled portions of tubes 84 and 90. As in conventional laboratory pipette filling adaptors, by making the tube walls at least about 3 millimeters thick but still yieldable, the valve seats will deform when opposed portions of the tube around them are manually pinched toward each other, and in such deformation at least one section of the seat will be forced away from the valve ball. This opens the valve. Releasing the pinch permits the valve seat to return to ball-gripping engagement over its entire periphery and this keeps the valve closed.

The apparatus of FIGS. 1 through 3 is placed in operation by connecting it to a source of dialyzate at 76 as well as to dialyzate removal means at 52, and to a source of blood or other liquid to be dialyzed at 28 as well as to a return for such liquid at 26.

For measuring ultrafiltration, the dialyzer preferably has its dialysis chambers and passageways first filled with dialyzate, following which a volume of air is introduced into chamber 31 by operation of the air injector 70. Such operation is easily effected by pinching tube 84 at valve 91 and squeezing bulb 88. The bulb can be dimensioned so that one squeeze will inject a suitable quantity of air into bore 78 and from there by way of connector 51 into chamber 31. Valve 91 can then be released to cause it to close, and it is sometimes helpful to tilt the apparatus to help move the large air bubble into chamber 31. After valve 91 is closed, valve 92 can be opened momentarily to permit the bulb to expand and suck in a fresh supply of air through filter 94. This places the apparatus in condition for the next injection of air.

The connection between connector 76 and the dialyzate source is preferably closed as by a shut-off valve, when the air injection is taking place. This will assure that the injected air is not carried by incoming dialyzate too far through dialyzer 10 to permit the desired measurement of ultrafiltration rate. The introduction of dialyzate into the dialyzer is also shut off when that measurement is being made.

Immediately after the injected air reaches chamber 31 it rises to the top of that chamber. If the dialyzer is maintained generally upright the air will not only reach the top of chamber 31 but it will also move into the upper portion of passageway 32 and part way down that passageway until the height occupied by the air is about the same in that passageway as in that chamber. This leaves the liquid level in passageway 32 relatively low so that the volume of ultrafiltrate that can be measured by downward movement of that water level is limited.

If the volume of air injected is kept small so as to provide a high liquid level in passageway 32, then the liquid level in chamber 31 is also relatively high and liquid from that chamber will spill over into the passageway after a very limited amount of ultrafiltration. Such spill-over makes it impossible to subsequently measure ultrafiltration rate by liquid level changes.

To avoid such limitation the dialyzer can be tilted when the introduced air has risen. The degree of tilt is such that it causes liquid to flow from near the tilted upper end of chamber 31 into the tilted upper end of passageway 32. In this way the liquid levels can be adjusted so that after restoring the dialyzer to its upright position, they are generally in positions such as shown at 37, 38 in FIG. 2.

So long as the blood or other liquid being dialyzed flows through the hollow fibers, ultrafiltration takes place causing water to move from the liquid being dialyzed through the walls of the fibers. As a result there will be a gradual increase in volume of the dialyzate around the fibers in chamber 31 and the air bubble will move down into passageway 32. In FIG. 2 the dialyzate level 37 in passageway 32 is starting its slow traverse through that passageway. That traverse is easily measured with an ordinary watch or clock have a seconds hand. A stopwatch can be used but is not necessary inasmuch as the measurement times can be 30 seconds or longer and split-second timing does not add much to the measurement accuracy.

The traverse of level 37 can be measured from the time it leaves the level of the floor 42 of header 16, to the time it reaches the top 45 of header 14. It is preferred however to apply a scale alongside passageway 32, as by means of a label 69 cemented onto the outside of the dialyzer casing. Inasmuch as a label is generally used to carry instructions as to the connections made to the dialyzer, the ultrafiltration-measuring scale can be conveniently added to such a label. The presence of a scale also enables the making of two or more successive measurements during a single traverse of the gas bubble through passageway 32.

Inasmuch as the ultrafiltration rate essentially depends on the difference between the pressures on the inside and outside of the hollow fibers, those pressures should be adjusted to the values at which the ultrafiltration rate is to be measured, and should not be changed during the measurement. The presence of a gas bubble in chamber 31 and the traverse of part of the bubble into passageway 32 will not significantly affect either of the critical pressures.

Blood is generally under a superatmospheric pressure of a hundred or so tor when it is being dialyzed, although that pressure can range from a low of about 30 tor to a high of about 160 tor or even higher. The dialyzate is generally under a subatmospheric pressure of about minus 50 to about minus 100 tor but can range from almost zero to an extreme of about minus 350 tor. While it is not essential to have the dialyzate at subatmospheric pressure, the use of subatmospheric pressure speeds up ultrafiltration. As a matter of precaution the dialyzate pressure is substantially below the pressure at which the blood is supplied, to keep dialyzate from entering the blood stream in the event there is a leak in the dialyzer. To maintain subatmospheric pressure in the dialyzate the dialyzer's dialyzate outlet 52 is preferably maintained in connection with the dialyzate supply system that develops such negative pressure.

Figure 6:
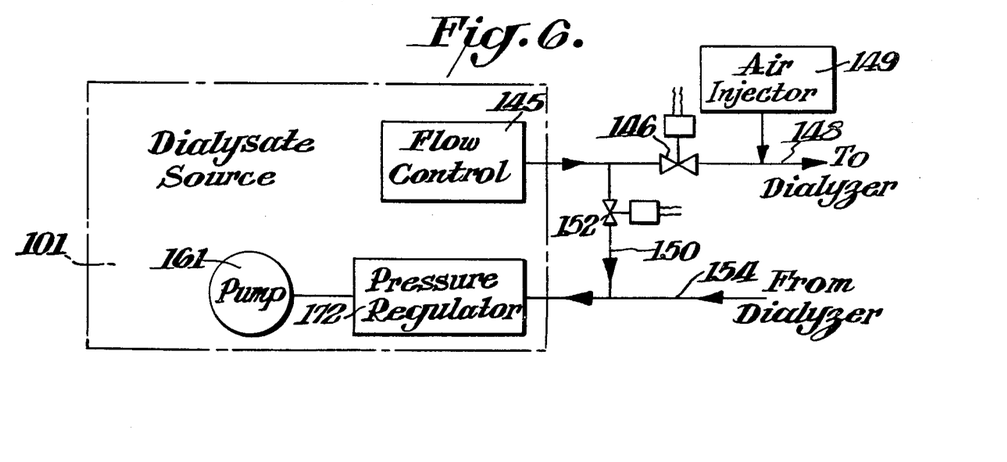
FIG. 6 is a diagrammatic representation of a portion of dialysis apparatus representative of the present invention.

FIG. 6 shows the key features of a typical dialyzate supply system modified to incorporate the gas injection of the present invention. A dialyzate source 101 which can have the usual components such as a water intake, heater, deaerater, proportioning mixer for dialyzate concentrate, etc. is arranged to prepare fresh dialyzate, and deliver it to supply line 148 where it flows to a dialyzer. The dialyzate source is also arranged to pump the used dialyzate from the dialyzer under subatmospheric pressure, receiving the used dialyzate in line 154 connected through a pressure regulator 172 to the intake of a pump 161 that can discharge to drain. The pressure regulator is adjusted to keep the desired subatmospheric pressure for the dialyzate as it passes through the dialyzer, and a flow control 145 in line 148 can be arranged to adjust the rate of dialyzate flow through the dialyzer. The pressure regulation can be manual or it can be automatically responsive to departures from a pre-set pressure, such as a pressure determined to be desirable for the ultrafiltration, or for a desired rate of ultrafiltration. Also the pressure regulator can be inserted in the dialyzate supply line 148, and the flow control in the dialyzate return line 154, if desired.

A solenoid-controlled shut-off valve 146 is included in line 148 and downstream of that valve the line can terminate in a standard dialyzate supply connector which mates with connector 51 (FIG. 1) and can be constructed like connector 74 (FIG. 1). At the connector or anywhere between it and valve 146, an air injector unit 149 branches off from line 148. That injection unit can be along the lines of injector 70 (FIG. 1).

A by-pass line 150, normally closed by a solenoid-controlled shut-off valve 152, branches from line 148 upstream of valve 146 and joins up with dialyzate return line 154 which can be supplied through another standard connector with dialyzate discharged by the dialyzer. The discharge-receiving connector mates with the dialyzer outlet connector 52 (FIG. 1) and can correspond to the connector in line 148.

The dialyzate supply system of FIG. 6 can be placed in operation by first connecting it to a dialyzer, closing supply valve 146 and opening by-pass valve 152, after which the various lines are filled, the pump 161 energized along with the heaters, etc., to establish appropriate dialyzate flow at the desired rate through by-pass line 150. Both valves 146 and 152 can be connected for operation by a single switch that closes one valve when it opens the other.

When suitable dialyzate flow through by-pass line 150 is attained, valve 152 is closed and valve 146 is opened to now direct the dialyzate stream through the dialyzer. Dialysis can then commence.

In the dialysis of blood it is sometimes desirable to start with a period of ultrafiltration in which there is little or no dialysis. For such operation the dialyzate stream through the dialyzer can be started as above indicated until the dialyzate chambers and passageways in the dialyzer are filled with dialyzate. The dialyzate flow into the dialyzer is then stopped by closing supply valve 146 and opening by-pass valve 152. The suction in line 154 remains in communication with the dialyzate in the dialyzer and this suction is maintained at the level desired for the ultrafiltration. When normal dialysis is to be applied it is only necessary to close by-pass valve 152 and open supply valve 146. When the pressure regulator is of the manual type, and sometimes even when it is of the automatic type, pressure adjustment may be needed when switching to and from by-pass operation.

The rate of ultrafiltration can be measured by injecting a quantity of air or other gas into the dialysis chamber 31 from injector 149. Valve 146 can be closed during such injection or shortly thereafter, to trap the gas in approximately the location shown in FIG. 2, and the rate measurement then carried out as described above.

A feature of such measurement is that it does not depend upon the use of a standard flowmeter with the very low liquid flow rates that are involved. In a one square meter dialyzer for example, ultrafiltration rates of only a few milliliters per minute are involved, sometimes as little as one milliliter per minute, and for such rates the flowmeters called for in U.S. Pat. No. 3,990,973, are not very accurate in addition to being subject to serious misoperation by the presence of even a small amount of non-liquid contamination.

The amount of ultrafiltration can also be followed by weighing the patient whose blood is being ultrafiltered, or by other techniques such as described in U.S. Pat. No. 4,008,712, but these are indirect techniques that also have a low accuracy and involve much more complexity.

The ultrafiltration rate measurement of the present invention can also be made in passageway 34 instead of or in addition to the measurement in passageway 32. The bubble of air initially injected into chamber 31 will gradually work its way into the top of chamber 33 as a result of ultrafiltration alone, or can be quickly moved to that location by opening the dialysis supply valve 146, and rate measurements can then be made in passageway 34 by the same techniques already described in connection with passageway 32. A second scale can then be applied to the dialyzer for use with passageway 34 measurements.

Ultrafiltration flow through passageway 34 results from ultrafiltration that takes place in chamber 31 as well as in chamber 33, and so is twice as fast as ultrafiltration flow through passageway 32. In general such passageways with cross-sectional areas between about ⅛ to about 3 square centimeters for each square meter of dialysis membrane surface through which the rate of ultrafiltration is to be measured, can be conveniently used for accurate rate measurement. Such passageways should be substantially free of capillarity and surface tension problems that would interfere with accurate reading of dialyzate levels. Thus the passageways are best at least about 4 millimeters wide in their narrowest aspect, and entirely devoid of solid contents.

Constructing the gas injector in the form of an attachment as at 70 in FIG. 1, makes it very adaptable for use with different dialyzate-supply systems. This adaptability is increased by incorporating dialyzate valving structure in the attachment, and FIGS. 4 and 5 illustrate such modifications.

Figure 4:
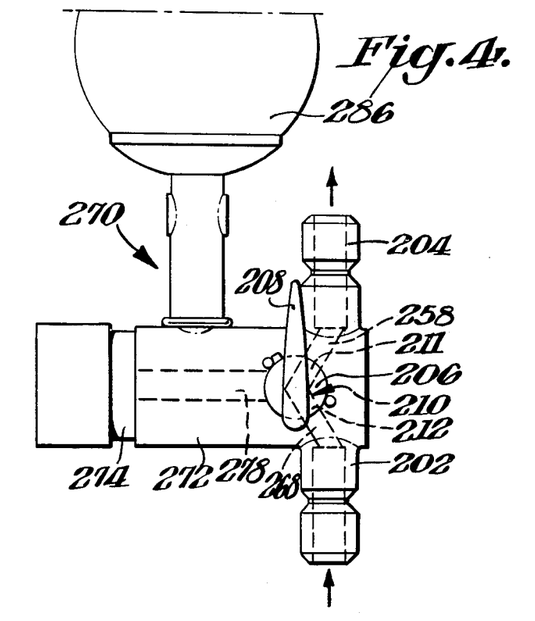
FIGS. 4 and 5 are front elevations of modified forms of attachment units for a dialyser and in accordance with the present invention.
Figure 5:
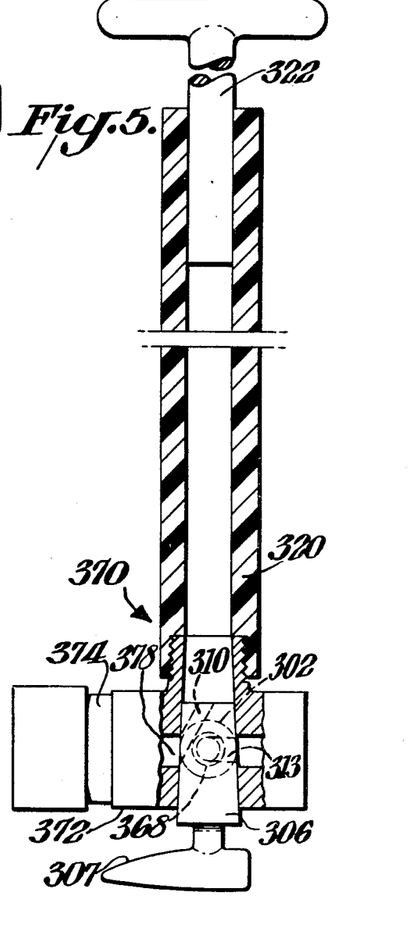

FIG. 4 shows an attachment 270 having an air injector 286 that can be identical to injector 86 of FIG. 1, fitted on a valve body 272 that carries a standard female dialyzate connector 274 and two standard male dialyzate connectors 202,204. The valve body receives a rotatable tapered valve plug 206 provided with a handle 208 by which the valve plug can be rotated around its longitudinal axis.

A generally L-shaped aperture 210 extends transversely through an intermediate portion of the plug, and has two openings 211, 212 respectively that can be brought into communication with passageway 278 or ports 268 and 258. Passageway 278 leads to connector 274, while ports 268, 258 separately open into connectors 202 and 204 respectively. Aperture 210, passageway 278 and ports 268 and 258 are arranged so that rotation of the valve plug will bring it to a position as illustrated in FIG. 4 in which it establishes communication between ports 268 and 258 but keeps both ports out of communication with passageway 278 and closes off that passageway.

The valve arrangement also enables the valve plug to be turned to a position 120 degrees clockwise from that illustrated, in which it establishes communication between port 268 and passageway 278, but closes port 258 from communication with either one.

Attachment 270 is conveniently used by connecting connector 274 with the dialyzate receiving connector of a dialyzer, connecting connector 202 with a dialyzate supply, and connecting connector 204 to the dialyzate return line. The dialyzate discharge connector of the dialyzer is also connected to that return line. Placing the valve in the illustrated position then establishes a dialyzate by-pass path, so that it is not necessary in this embodiment to use a dialyzate supply system that has its own by-pass.

Valve 206 can then be used to admit dialyzate to the dialyzer and prepare for gas injection from injector 270. After the injection the valve is turned to by-pass position, the ultrafiltration rate measured, and dialysis can then be effected by merely rotating the valve back to dialysis position where it supplies dialyzate to the dialyzer.

If desired the air injector can be a simple vent that can be opened to the atmosphere. Inasmuch as the dialyzate line is kept at subatmospheric pressure whenever dialyzate is supplied, it is only necessary to open the line to the atmosphere and thus bleed a little air into the supplied dialyzate, when the ultrafiltration rate is to be measured.

FIG. 5 shows a vent-type construction in an attachment 370. This attachment has a valve body carrying a standard dialyzate connector 374 that opens into a passageway 378 leading to the rotatable plug 306 of a plug valve 307. Also communicating with plug 306 is a port 368 that leads to a standard connector 302 for a dialyzate supply.

Valve plug 306 has a first aperture 310 extending from a side of the plug to its deep end, and a second aperture 313 in the shape of a transverse L positioned to establish communication between port 368 and passageway 378 when the plug is turned to the appropriate position. When so turned aperture 310 does not open to either port 368 or passageway 378, but when the plug is turned 90 degrees counter-clockwise looking at it from its handle end, it is in the position shown in the drawing and aperture 310 then opens onto passageway 378. In this position port 368 is not in communication with passageway 378.

The deep end of aperture 310 can merely be exposed to the atmosphere, preferably through a filter, but as illustrated valve body 372 also carries a syringe barrel 320 and piston 322. Barrel 320 opens onto the deep end of the valve plug, and piston can be pre-set to a position in the barrel that provides a pre-determined volume of air in the barrel. This is readily accomplished as by inserting the piston in the barrel, rotating the valve plug to a position that opens the barrel to an air discharge port, pushing the piston to the pre-determined level, and then turning the valve plug to close off the air discharge port. Such air discharge port can be in the valve body 372 directly opposite port 368, for example.

When attachment 370 is in use and the valve plug is turned to the illustrated position after the piston 322 is placed in its pre-determined position, the flow of dialyzate to the dialyzer is cut off and the air in barrel 320 is sucked into the dialyzate in the dialyzer. This carries piston 322 into the barrel as far as it will go, at which point the piston effectively seals off aperture 310. The ultrafiltration rate can then be measured and when desired dialysis is initiated or resumed by rotating valve plug 306 to the position at which it permits dialyzate flow through the dialyzer.

It is also practical to provide the valve body with an additional port leading to a connection for returning dialyzate to the return line of a dialyzate supply system. Such an additional port can for instance be directly opposite passageway 378 so that when the valve plug is in the position illustrated it establishes a dialyzate by-pass path.

Figure 7:
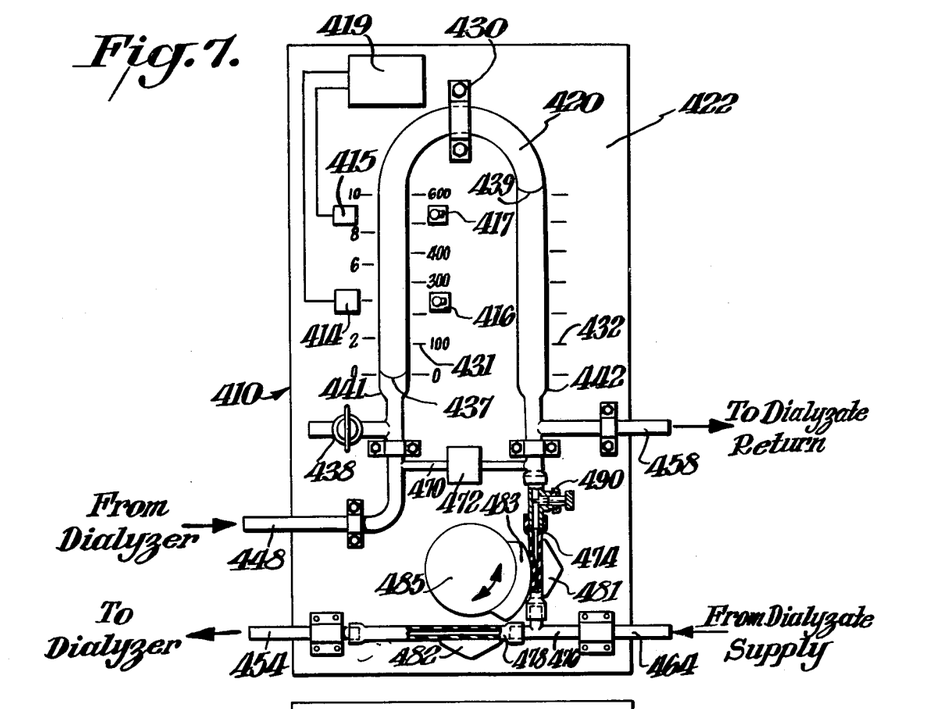
FIG. 7 is a front elevation of a different portion of a dialysis apparatus pursuant to the present invention.

FIG. 7 shows a further modification of the ultrafiltration measurement of the present invention. This modification takes advantage of the accuracy obtained with the liquid level traverse rate timing technique, and uses an attachment 410 that can be inserted in the dialyzate lines 454, 448 of any dialyzer.

Attachment 410 is essentially an inverted U-tube 420 mounted as by mounting straps 430 on a support 422 that can carry scale markings 431, 432 for each leg 441, 442 of the tube. Leg 441 is also shown as connected to an air-injector which can be a syringe or valve 438 manually operable to cause a bubble of air to be sucked into tube 420. Such bubble will rise to the top of tube 420 and most of the bubble will occupy leg 442, leaving very little transit space in either leg. To move the bubble so that its opposite ends are at locations suitable for maximum transit travel, as indicated at 437, 439, the entire attachment 410 can be tilted to cause the bubble to move into leg 441, and then the attachment is restored to the illustrated position.

Alternatively the air-injection site can be shifted to a location far enough upstream in line 448 to permit the injection of a suitably-sized air bubble before the bubble reaches the position under the leg 441 of the U-tube. This alternative does not require tilting of the apparatus.

A different alternative is to connect the bottoms of the U-tube legs with a level equalizer 470 having a closure 472 such as a valve, or if the equalizer is made of yieldable tubing, a clamp or hemostat. Momentarily opening the closure 472 after the injection of a bubble causes the bubble to distribute itself equally between both legs of the U-tube. This alternative enables level transit measurement along the upper portion of leg 441 and along the lower portion of leg 442.

Automatic measuring of the transit can be effected as by the photoelectric level sensors shown at 414, 415. Light bulbs 416, 417 illuminate the tube legs alongside the sensors and cause the sensors to generate a pulse as the liquid level passes through the light path from bulb to sensor. The sensors are shown connected to a measuring unit 419 that measures the time elapsing between the pulses and gives a reading in milliliters per minute of ultrafiltration.

The apparatus of FIG. 7 also includes a dialyzate by-pass circuit and control. Thus the bottom of U-tube leg 442 not only carries a dialyzate return line connection 458, but it also connects through a yieldable tube 474 with a dialyzate supply tube 476 carrying a supply connector 464 for connection to a source of dialyzate and also carrying a second yieldable tube 478 running to line 454 that supplies dialyzate to a dialyzer.

Yieldable tubes 474, 478 are positioned alongside rigid stops 481, 482 against which they can be squeezed by lobe 483 of rotary cam 485. The cam is shown in the position in which it pinches tube 474 shut but leaves tube 478 open, so that dialyzate can flow from the dialyzate source to the dialyzer, and from the dialyzer to the dialyzate return through line 448, U-tube 420, and return connector 458. Equalizer tube 470 has its closure 472 closed when it is not equalizing an injected bubble, but even if that closure is left open the equalizer tube can be of such small bore, i.e. about 1/16 inch, that only a very small fraction of total dialyzate flow will go through it.

FIG. 7 also shows an adjustable valve 490 fitted to yieldable tube 474 so that the flow of dialyzate through that tube can be accurately controlled when cam 485 opens the tube to establish a dialyzate by-pass. Such control is generally needed when there is no automatic control of the dialyzate pressure.

The apparatus of FIG. 7 is placed in operation by connecting it in a dialyzate supply circuit, filling all parts of the dialyzate path with dialyzate, introducing into the dialyzer the liquid to be dialyzed, and rotating cam 485 so that it stops dialyzate flow through tube 478 but opens dialyzate by-passing through tube 474. Valve 490 can then be adjusted to bring the dialyzate pressure to the desired valve. Shifting the dialyzate flow from the normal path through the dialyzer, to the by-pass path, changes the resistance to dialyzate flow and can cause an undesired change in the dialyzate pressure if the dialyzate supply does not have an automatic pressure control with the desired operating tolerance. Any departure of the dialyzate pressure during ultrafilteration measurement from the pressure used during dialysis will yield a measurement that does not indicate the rate at which ultrafiltration takes place during the dialysis.

When the pressure is adjusted the air bubble is injected into tube 420, its level adjusted if needed, and the movement of the level timed.

Figure 8:
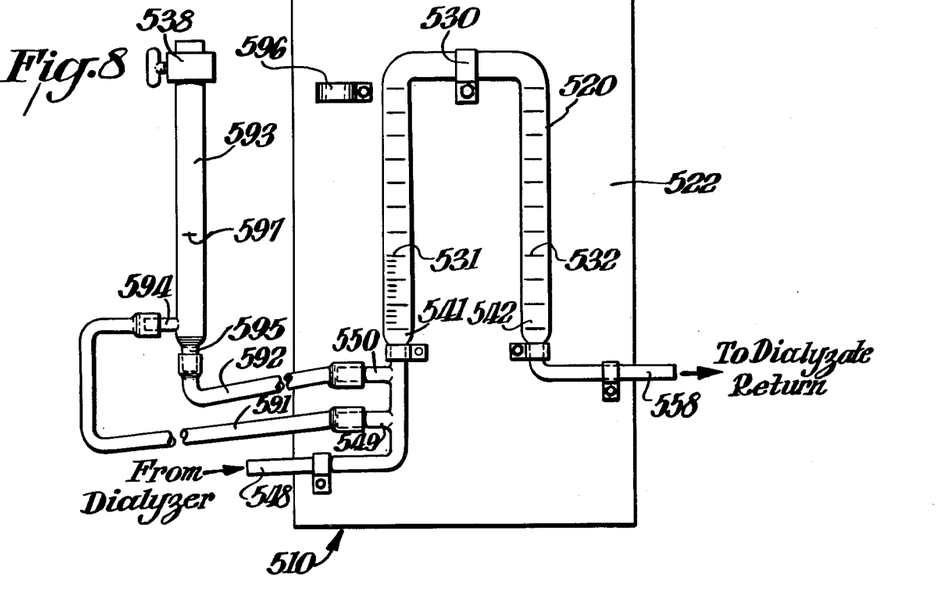
FIG. 8 is a similar view of a modification of the construction of FIG. 7.

FIG. 8 illustrates a simple ultrafiltration measuring unit 510 that is merely inserted in a dialyzate return line and can be used with a dialyzate by-pass contained in the dialyzate source (as in FIG. 6). Unit 510 has an inverted U-tube 520 held by clips 530 on a board 522, and marked along its legs 541, 542 with scales 531, 532. Leg 542 opens only to a dialyzate return connection 558, but leg 541 has three inlets 548, 549, 550. Inlet 548 is the connector to which the dialyzate is delivered from the return line of a dialyzer, and inlets 549 and 550 connect through flexible tubes 591, 592 to a gas injector 593.

Injector 593 is an elongated chamber having at its upper end a valve 538 or the like that permits air to be sucked into the chamber. Nipples 594, 595 at the other end of the injector chamber receive the tubins 591, 592. The board 522 can also be provided with a spring-clip holder 596 into which the gas injector can be inserted and retained when not in use.

The apparatus of FIG. 8 is operated by connecting it into the dialyzate circuit, filling it with dialyzate, and placing the dialyzate in by-pass flow. It is generally necessary to lower the injection chamber 593 and turn it upside down in order to fill the apparatus completely, the inversion causes any gas in the chamber as well as in tubings 591, 592 to bubble up into the U-tube and from there to be exhausted with the dialyzate return.

A desired volume of air or any suitable gas is then introduced through injector 538 into chamber 593, while the chamber is held upright, although this step can alternatively be carried out before the dialyzate is placed on by-pass, and even before any dialyzate flow is initiated. An indicator marking such as 597 can be carried by the chamber to show the desired gas volume.

The gas in chamberr 593 is then transferred to leg 541 of the U-tube, by appropriately tilting and lowering chamber 593. By reason of the two connections between the chamber and that U-tube leg, the gas will be mostly confined to that leg. Liquid displaced from U-tube leg 541 by the incoming gas moving through the lower inlet 549, down into the chamber to take the place of the gas moving out of the chamber. The result is that the liquid level in leg 541 or in both legs 541 and 542 is at a location that enables the measurement of considerable traverse travel.

It is not essential that dialyzate be in by-pass flow in order to effect ultrafiltration measurement. So long as the pressure on the dialyzate in the dialyzer is maintained at the value at which ultrafiltration is to be measured, the by-pass flow can be partially or completely interrupted. Thus a manual or automatic pressure control is all that is needed providing appropriate suction, such as the intake of a pump, is being applied.

When measuring ultrafiltration rates downstream from a dialyzer, the tubing at which measurement readings are taken generally have bores that are generally 6 or more millimeters wide. The U-tubes of FIGS. 7 and 8 are accordingly shown as having larger bores than the tubing to which they are connected. However, all of the tubing can be of the same bore as the U-tubes, if desired.

The ultrafiltration rate can also be measured by other accurate means such as displacement or turbine type rotors inserted in the dialyzate flow line and rotated by the dialyzate flow to generate an electric voltage indicative of the flow rate. Such voltage generation can be by means of an electric generator, or of contacts that are momentarily closed at each revolution of the rotor to give a series of electrical pulses from a battery or the like. These pulses are then integrated as by means of a small transistor amplifier to yield a voltage indicative of the pulse rate. Such flow rate measuring devices are shown by way of example in U.S. Pat. Nos. 3,792,610 and 3,783,248.

Two such accurate instruments can be used, one in the dialyzer's dialyzate discharge line and the other in its dialyzate supply line to separately measure the dialyzate flow rates in those lines and thus show by the difference between those rates how fast ultrafiltration adds liquid to the dialyzate. In this way ultrafiltration can be measured while dialysis is being effected.

For greater accuracy the two measuring instruments can be combined to provide a differential measuring arrangement. Thus a single small electric generator can have its armature connected for rotation by the dialyzate entering the dialyzer, and its field connected for rotation in the same direction by the dialyzate leaving the dialyzer. The voltage output of the generator will then directly show the ultrafiltration rate.

Alternatively a set of make-and-break points can be rotated by one dialyzate stream and a breaker cam rotated in the same direction by the other dialyzate stream, the resulting pulses of current through the points indicating the ultrafiltration rate.

Where it is desired to effect ultrafiltration at a generally constant rate, the signals showing the ultrafiltration rate can be connected to electrically adjust the pressure regulator 172 for example. Thus these signals can increase the pressure on the dialyzate when the ultrafiltration is faster than a predetermined rate, and can decrease the pressure when the ultrafiltration is too slow.

The voltage output of the above-mentioned electric generator, or the average output of the make-and break pulses, can for this purpose be supplied to a transistor amplifier biased at the voltage that is set for the desired ultrafiltration rate. By supplying the amplifier's output to a servo motor connected to a pressure-regulator-adjusting screw, the dialyzate pressure will be raised when the ultrafiltration-indicating voltage is above the bias level, and lowered when that voltage is below that level.

The ultrafiltration rate signals can also be integrated with respect to time so that they show the total volume of ultrafiltration liquid added to the dialyzate and thus separated out from the blood of a patient being dialyzed. The signals of the electric generator need only be passed through an integrating circuit for this purpose, and the make-and-break pulses need only be counted as by a simple pulse counter.

The integrated output or the counter can be set to trigger a buzzer and/or light an indicator lamp when a pre-determined amount of ultrafiltration volume is accumulated. Patients being dialyzed generally require different amounts of water loss to compensate for their varying water accumulation or water intake during kidney disfunction, and it is helpful to preset a buzzer or lamp circuit for automatically indicating such compensation.

What is claimed is:

1. An ultrafiltration-measuring unit having an inverted transparent U-tube, connection means at each end of the tube for inserting the tube in series in a dialyzate discharge line of a dialyzer to convey all the dialyzate discharged, bubble-injection means connected for injecting a bubble of gas into the tube, means for bringing the level of dialyzate at one end of the bubble into flow-reading position, and markings along at least one leg of the tube to indicate different liquid levels.

2. In the process of measuring the rate of ultrafiltration in a dialysis unit containing a dialysis chamber, the improvement according to which the dialysis unit is tiltable, there is incorporated in that unit an externally viewable vertically positionable dialyzate flow passageway downstream and in series with the dialysis chamber to carry off the entire dialyzate outflow from that chamber, said dialyzate flow passageway being sufficiently narrow and empty to enable accurate reading of the level of liquid moving through it, circulating through the unit a liquid to be dialyzed, introducing dialyzate into the dialyzate section of the dialysis chamber and into said dialyzate flow passageway to partially fill that passageway with the dialyzate, terminating said dialyzate introduction, holding the unit with that passageway generally vertical so that the liquid level in the partially filled passageway moves downstream along the length of the passageway as ultrafiltration takes place from the liquid to be dialyzed, and timing the movement of that level.

3. The combination of claim 2 in which the partial filling of the passageway is effected by first substantially filling it, and then introducing a quantity of gas into the dialysis chamber to displace some of the dialyzate and position the liquid level in the passageway.

4. The combination of claim 3, in which the passageway is alongside the dialysis chamber, the unit is inverted while the gas is introduced so as to move most of the introduced gas upstream of the passageway, and the unit is then returned to ultrafiltration-measuring position.

5. An ultrafiltration-measuring attachment for a dialyzer, said attachment having (a) a standard dialyzate conduit connection containing a length of conduit and connection means by which the attachment and the conduit can be connected directly to the dialyzate inlet of a dialyzer,
(b) a bubble injector in communication with the conduit for introducing a predetermined volume of gas through the conduit and into the dialyzer,
(c) a valve that closes said communication and that can be opened to effect the gas introduction, and
(d) a second standard dialyzate conduit connection communicating with the conduit.

6. The combination of claim 5 in which the attachment also contains a third standard dialyzate connector in valved communication with the second connector.

* * * * *